United States Patent [19]

Yoshitake

[11] Patent Number: 5,089,620

[45] Date of Patent: Feb. 18, 1992

[54] CERTAIN 3-NITRO-PYRIDYL AMINO METHYL SILANES AND SILOXANES

[75] Inventor: Makoto Yoshitake, Ichihara, Japan

[73] Assignee: Dow Corning Toray Silicone Company, Ltd., Tokyo, Japan

[21] Appl. No.: 697,389

[22] Filed: May 9, 1991

Related U.S. Application Data

[62] Division of Ser. No. 540,668, Jun. 18, 1990, Pat. No. 5,041,589.

[30] Foreign Application Priority Data

Jun. 21, 1989 [JP] Japan .................................. 1-158719

[51] Int. Cl.⁵ .............................. C07F 7/10; C07F 7/18
[52] U.S. Cl. ....................................... 546/14; 556/424
[58] Field of Search ............................................ 546/14

[56] References Cited

U.S. PATENT DOCUMENTS 3,847,860 11/1974 Seiler et al. ......................... 524/262

Primary Examiner—Alan L. Rotman
Attorney, Agent, or Firm—Roger E. Gobrogge

[57] ABSTRACT

The present invention relates to novel organosilicon compounds and a method for their preparation. More particularly, the present invention relates to novel organosilicon compounds which are synthesized from triorganosilylmethylamine (or derivatives thereof) and a nitro group-substituted aromatic halide, as well as a method for the preparation of these novel organosilicon compounds.

1 Claim, No Drawings

CERTAIN 3-NITRO-PYRIDYL AMINO METHYL SILANES AND SILOXANES

This is a divisional of copending application Ser. No. 07/540,668 filed on Jun. 18, 1990 now U.S. Pat. No. 5,041,589.

BACKGROUND OF THE INVENTION

The present invention relates to novel organosilicon compounds and a method for their preparation. More particularly, the present invention relates to novel organosilicon compounds which are synthesized from triorganosilylmethylamine (or derivatives thereof) and a nitro group-substituted aromatic halide, as well as a method for the preparation of these novel organosilicon compounds.

SUMMARY OF THE INVENTION

The present invention relates to organosilicon compounds as represented by the following general formula:

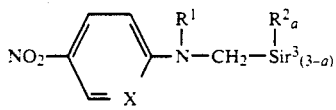

wherein $R^1$ is selected from the group consisting of hydrogen and a monovalent hydrocarbon group having 1 to 10 carbon atoms; each $R^2$ is independently a monovalent hydrocarbon group having 1 to 10 carbon atoms; $R^3$ is an alkoxy group having 1 to 10 carbon atoms; X is selected from the group consisting of:

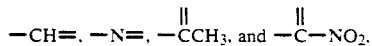

and a is an integer with a value of zero to 3.

The present invention also relates to a method of preparing the above compounds comprising the execution of a dehydrohalogenation reaction between (A) triorganosilylmethylamine as represented by the following general formula

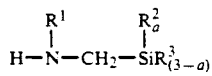

wherein $R^1$ is selected from the group consisting of hydrogen and a monovalent hydrocarbon group having 1 to 10 carbon atoms; each $R^2$ is independently a monovalent hydrocarbon group having 1 to 10 carbon atoms; $R^3$ is an alkoxy group having 1 to 10 carbon atoms; and a is an integer with a value of zero to three, or a derivative thereof, and (B) a nitro group-substituted aromatic halide as represented by the following general formula:

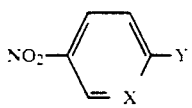

wherein X is an organic group selected from the group consisting of:

and Y is a halogen atom selected from the group consisting of fluorine, chlorine, bromine, and iodine in the presence of (C) a hydrogen halide acceptor.

DETAILED DESCRIPTION OF THE INVENTION

The present invention is based on the discover of novel organosilicon compounds of the formula:

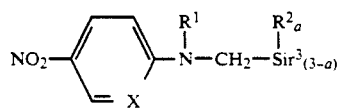

The group $R^1$ in the preceding formula is selected from the group consisting of the hydrogen atom and monovalent hydrocarbon groups having 1 to 10 carbon atoms as exemplified by alkyl groups such as methyl, ethyl, propyl, butyl, pentyl, hexyl, heptyl, octyl, etc.; aryl groups such as phenyl, naphthyl, etc.; and aralkyl groups such as benzyl, phenethyl, etc. The group $R^2$ comprises the same or different monovalent hydrocarbon group(s) having 1 to 10 carbon atoms as exemplified by alkyl groups such as methyl, ethyl, propyl, butyl, pentyl, hexyl, heptyl, octyl, etc.; aryl groups such as phenyl, naphthyl, etc.; and aralkyl groups such as benzyl, phenethyl, etc. $R^3$ is an alkoxy group having 1 to 10 carbon atoms as exemplified by methoxy, ethoxy, propoxy, butoxy, pentyloxy, hexyloxy, heptyloxy, octyloxy, etc. X is an organic group selected from

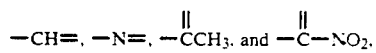

and a is an integer with a value of zero to three.

This organosilicon compound is concretely exemplified by the following compounds.

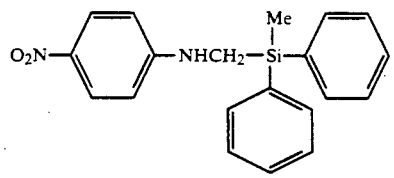

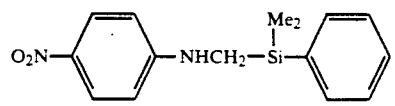

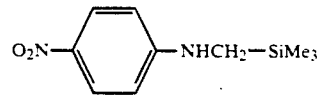

-continued

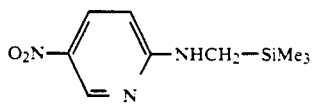

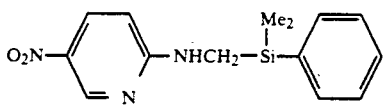

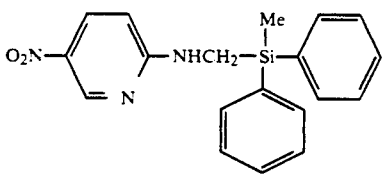

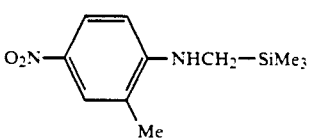

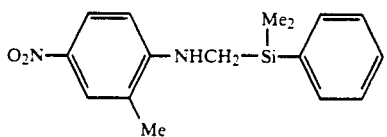

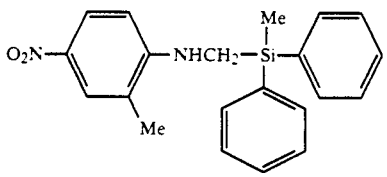

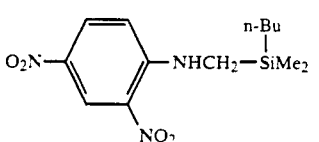

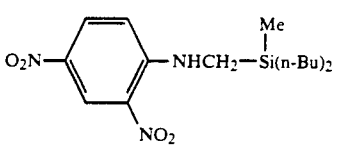

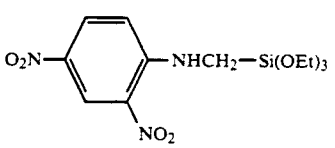

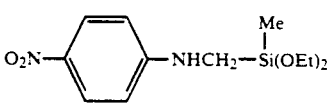

The present invention is also based on the discovery of a novel method of manufacturing these organosilicon compounds comprising: the execution of a dehydrohalogenation reaction between (A) triorganosilylmethylamine as represented by the following general formula

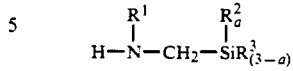

wherein $R^1$ is selected from the group consisting of hydrogen or a monovalent hydrocarbon group having 1 to 10 carbon atoms; each $R^2$ is independently a monovalent hydrocarbon group having 1 to 10 carbon atoms; $R^3$ is an alkoxy group having 1 to 10 carbon atoms; and a is an integer with a value of zero to three, or a derivative thereof. and (B) a nitro group-substituted aromatic halide as represented by the following general formula:

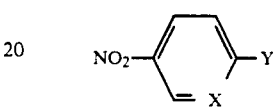

wherein X is an organic group selected from the group consisting of

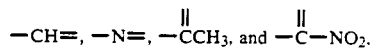

and Y is a halogen atom selected from the group consisting of fluorine, chlorine, bromine, and iodine in the presence of (C) a hydrogen halide acceptor.

The main starting material in this synthesis of the organosilicon compound of the present invention is the triorganosilylmethylamine or derivative thereof comprising the component (A) used in the aforesaid method. The groups $R^1$, $R^2$, and $R^3$ in the preceding formula are respectively defined as for the groups $R^1$, $R^2$, and $R^3$ in the organosilicon compounds of the present invention. The compounds comprising this component (A) and their reactivities are well known. For example, it has been reported that the basicity of trimethylsilylmethylamine is approximately 5 times that of its analogue, neopentylamine (J. Am. Chem. Soc., 73, 5130 (1951)). It has also been reported that the oxidation potential is lower when the triorganosilylmethyl group is bonded to a nitrogen atom than in the corresponding silicon-free compound and that a characteristic oxidation reaction occurs (J. Organomet. Chem., 29, 33 (1971)).

The nitro group-substituted aromatic halide comprising the component (B) used by this method participates in the formation of the organosilicon compounds of the present invention through a dehydrohalogenation reaction with the above component (A). Its reactivity depends on the species of halogen atom. Thus, with regard to the halogen atom in nitro group-substituted aromatic halides, the reactivity increases with declining atomic weight, and the reactivity increases in the sequence iodine compounds < bromine compounds ° chlorine compounds ° fluorine compounds. Accordingly, the organosilicon compounds of the present invention can be obtained in high yields when the maximally reactive fluorine compounds are used. However, the fluorine compounds are more expensive than the other halogen compounds, and thus from a practical standpoint are not always suitable for the preparative method of the present invention.

Examples of the hydrogen halide acceptor comprising the component (C) used by this method are tertiary amines such as triethylamine, pyridine, etc., and conjugate bases such as sodium carbonate, potassium carbonate, sodium acetate, etc.

While this reaction will proceed even in a solvent-free system, the execution of the reaction in an organic solvent is preferred in order to obtain good yields of the target compound. This organic solvent is not specifically restricted as long as it can dissolve the above-described components (A) and (B). Polar solvents are ideally used as this organic solvent, for example, amides such as N,N-dimethylformamide, N-methylpyrrolidone, etc., as well as dimethyl sulfoxide, hexamethylphosphonamide, and so forth.

The desired product can generally be rapidly obtained in good yields when this reaction is run by dissolving the two starting reactants (components (A) and (B)) in the organic solvent and heating this solution in the presence of the hydrogen halide acceptor comprising component (C). The reaction temperature is closely related to the reaction rate, and the reaction is completed more rapidly at higher temperatures. However, since side reactions tend to occur more readily when the reaction temperature is too high, an appropriate selection of the reaction temperature must be made. In concrete terms, the reaction is preferably conducted in the temperature range of 100 to 150 degrees Centigrade.

The reaction product can be isolated and purified by the methods generally employed for organic compounds. For example, in order to separate the salt formed by reaction of the hydrogen halide acceptor and the hydrogen halide produced in the reaction, water and organic solvent are added to the solution after the reaction and this is shaken. Or, organic solvent is added to the reaction solution and the precipitate is separated by filtration. No particular restriction is placed on the organic solvent used at this point as long as it is immiscible with water and does not readily dissolve the salt. However, from the standpoints of extraction efficiency and facilitating salt separation, diethyl ether, ethyl acetate, etc., are ideally used. Many of the organosilicon compounds of the present invention are crystalline solids, which can be isolated and purified by recrystallization. However, in the case of an inherently low crystallinity, or in the absence of crystallization due to the presence of impurities in the components dissolved in the organic layer after the extraction process, a high-purity target material can still be obtained through purification by silica gel column chromatography. While there are no specific restrictions on the organic solvent used in this recrystallization, the following are ideally used: aliphatic hydrocarbon solvents such as n-hexane, cyclohexane, and so forth, and aromatic hydrocarbon solvents such as benzene, toluene, and so forth.

The molecular structure of the organosilicon compounds of the present invention can be confirmed by various analytic methods. For example, nuclear magnetic resonance spectral analysis, infrared absorption spectral analysis, ultraviolet absorption spectral analysis, etc., are extremely useful techniques for determining such information as the atomic arrangement and substitution pattern in the organosilicon compounds of the present invention. Moreover, techniques such as elemental analysis and liquid chromatography are useful for measuring the purity of the compounds.

The organosilicon compounds of the present invention as described above have potential applications as nonlinear optical materials. In other words, in each molecule of these organosilicon compounds, a strongly electron-withdrawing nitro group and a strongly electron-donating (triorganosilyl)methylamino group are bonded via a conjugated pi-system, on the basis of which the manifestation of unique or distinctive effects can be expected. In fact, it has been confirmed that some of the organosilicon compounds of the present invention exhibit second harmonic generation, a second-order nonlinear optical effect, in the crystalline state. Moreover, even with substances which do not exhibit second-order nonlinear optical effects in the crystalline state, it may be possible to obtain material exhibiting second-order nonlinear optical effects by means of, for example, inducing molecular orientation through voltage application within a suitable polymeric material and crystallization.

EXAMPLES

The present invention is explained below in greater detail with reference to illustrative examples. Parts denotes weight parts in these examples. However, the scope of the present invention is not specifically restricted by these illustrative examples.

EXAMPLE 1

15.8 Parts 4-chloronitrobenzene, 22.7 parts (diphenylmethylsilyl)methylamine, 11.1 parts triethylamine, and 80 parts N-methylpyrrolidone were mixed in a dried reactor and stirred with heating at 140 degrees Centigrade for 8 hours. After cooling, 200 parts ethyl acetate and 200 parts water were added to the reaction solution with thorough mixing. The solution separating as the upper layer was taken off and washed with water three times. Anhydrous sodium sulfate was added followed by vigorous shaking and then standing for 1 hour. The solid was separated off by filtration and the obtained solution was concentrated in vacuo. The components present in the residue were separated by silica gel chromatography (developer=mixed solvent of n-hexane and ethyl acetate). The separated yellow solution fraction was concentrated in vacuo, and the obtained solid was recrystallized from a mixed solvent of n-hexane and toluene to afford 17.8 parts yellow needle-form crystals (yield=51.1%). The molecular structure of this crystal was confirmed to be 4-N-(diphenylmethylsilyl)methylaminonitrobenzene (below) based on elemental analysis, nuclear magnetic resonance spectral analysis, and infrared absorption spectral analysis.

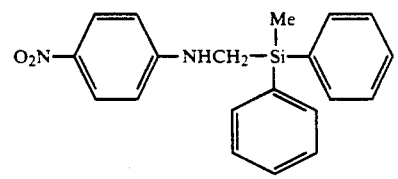

| Elemental analysis | C | H | N |
| --- | --- | --- | --- |
| calculated (%) | 68.93 | 5.78 | 8.04 |
| found (%) | 68.90 | 5.99 | 8.04 |

15.9 Parts 2-chloro-5-nitropyridine, 16.5 parts (dimethylphenylsilyl)methylamine, 15.2 parts triethylamine, and 80 parts N-methylpyrrolidone were mixed in a dried reactor and stirred while heating at 140 degrees Centigrade for 1 hour. After cooling, 200 parts ethyl acetate and 200 parts water were added to the reaction solution with thorough mixing. The solution separating as the top layer was taken off and washed three times with water. Anhydrous sodium sulfate was added followed by vigorous shaking and then standing for 1 hour. The solid was filtered off and the obtained solution was concentrated in vacuo to obtain a yellow solid. This was recrystallized from a mixed solvent of n-hexane and toluene to afford 2.12 parts yellow needle-like crystals (yield=73.8%). The molecular structure of this crystal was confirmed to be 2-N-(dimethylphenylsilyl)-methyl-5-nitropyridine (below) based on elemental analysis, nuclear magnetic resonance spectral analysis, and infrared absorption spectral analysis.

The obtained crystals were ground to a diameter of approximately 100 micrometers with a mortar, and approximately 20 mg of this ground material was fixed on a slide glass using cellophane tape. Pulses from a Nd:YAG laser were directed perpendicularly onto this sample, and a photomultiplier was used to measure the strength of the light at 530 nanometers (second harmonic) generated at a reflection angle of 45 degrees from the surface of the sample. It was determined that this light was 15 times stronger than that measured using urea as the sample.

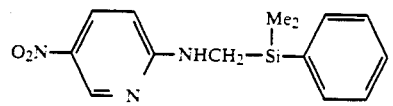

| Elemental analysis | C | H | N |
| --- | --- | --- | --- |
| calculated (%) | 58.33 | 6.21 | 14.62 |
| found (%) | 58.51 | 5.96 | 14.62 |

EXAMPLE 3

15.5 Parts 2-fluoro-5-nitrotoluene, 14.0 parts (trimethylsilyl)methylamine hydrochloride, 30.5 parts triethylamine, and 80 parts N-methylpyrrolidone were mixed in a dried reactor and stirred for 3 hours while heating at 120 degrees Centigrade. After cooling, 200 parts diethyl ether and 200 parts water were added to the reaction solution with thorough mixing. The solution separating as the top layer was separated off and washed 3 times with water. Anhydrous sodium sulfate was then added with vigorous shaking followed by standing for 1 hour. The solid was then filtered off and the obtained solution was concentrated in vacuo. The components in the residue were separated by silica gel chromatography using a mixed solvent of n-hexane and ethyl acetate as the developer. The separated yellow solution fraction was concentrated in vacuo to afford a solid, which was recrystallized from a mixed solvent of n-hexane and toluene to give 8.3 parts (34.8%) yellow plate-like crystals. The molecular structure of this crystal was confirmed as 2-N-(trimethylsilyl)methylamino-5-nitrotoluene (below) by elemental analysis, nuclear magnetic resonance spectral analysis, and infrared absorption spectral analysis.

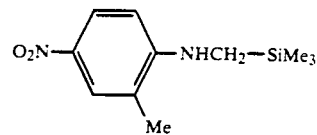

| Elemental analysis | C | H | N |
| --- | --- | --- | --- |
| calculated (%) | 55.43 | 7.61 | 11.75 |
| found (%) | 55.44 | 7.61 | 11.89 |

EXAMPLE 4

20.3 Parts 1-chloro-2,4-dinitrobenzene, 18.2 parts (n-butyldimethylsilyl)methylamine, 55.2 parts potassium carbonate, and 80 parts dimethyl sulfoxide were mixed in a dried reactor and stirred for 4 hours while heating at 100 degrees Centigrade. After cooling, 200 parts diethyl ether and 200 parts water were added to the reaction solution with thorough mixing. The solution separating as the upper layer was taken off and washed 3 times with water. Anhydrous sodium sulfate was then added with vigorous shaking followed by standing for 1 hour. The solid was filtered off and the obtained solution was concentrated in vacuo to afford a yellow solid. This was recrystallized from a mixed solvent of n-hexane and toluene to give 26.8 parts (yield =86.1%) yellow needle-like crystals. The molecular structure of this crystal was confirmed as 1-N-(n-butyldimethylsilyl)methyl-2,4-dinitrobenzene (below) based on elemental analysis, nuclear magnetic resonance spectral analysis, and infrared absorption spectral analysis.

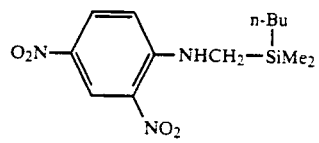

| Elemental analysis | C | H | N |
| --- | --- | --- | --- |
| calculated (%) | 50.14 | 6.80 | 13.49 |
| found (%) | 49.69 | 6.79 | 13.58 |

EXAMPLE 5

20.3 Parts 1-chloro-2,4-dinitrobenzene, 19.3 parts (triethoxysilyl)methylamine, 15.2 parts triethylamine, and 80 parts N-methylpyrrolidone were mixed in a dried reactor and stirred for 1 hour while heating at 140 degrees Centigrade. After cooling, 500 parts diethyl ether was added to the reaction solution with thorough mixing, and the precipitate was filtered off. The filtered solution was concentrated in vacuo to afford a thick yellow liquid. This was purified by silica gel chromatography using a mixed solvent of n-hexane and ethyl acetate as the developer. The separated yellow solution fraction was concentrated in vacuo to obtain a solid, which was recrystallized from a mixed solvent of n-hexane and toluene to give 7.8 parts (21.7%) yellow needle-like crystals. The molecular structure of this crystal was confirmed as 1-N-(triethoxysilyl)methyl-2,4-dinitrobenzene (below) by elemental analysis, nuclear magnetic resonance spectral analysis, and infrared absorption spectral analysis.

That which is claimed is:

1. Organosilicon compounds as represented by the following general formula

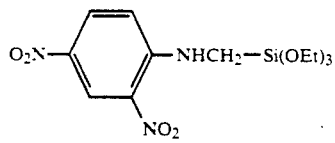

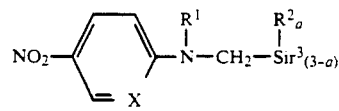

wherein $R^1$ is selected from the group consisting of the hydrogen atom and a monovalent hydrocarbon group having 1 to 10 carbon atoms, each $R^2$ is independently a monovalent hydrocarbon group having 1 to 10 carbon atoms, $R^3$ is an alkoxy group having 1 to 10 carbon atoms, X is $-N=$ and a is an integer with a value of zero to 3.

* * * * *